United States Patent
Dubrovskiy et al.

(10) Patent No.: US 12,357,610 B2
(45) Date of Patent: Jul. 15, 2025

(54) ARYL-SUBSTITUTED ACETAMIDE AND PYRROLIDIN-2-ONE DERIVATIVES AND THEIR USE FOR THE TREATMENT OF SEIZURES

(71) Applicant: University of Houston System, Houston, TX (US)

(72) Inventors: Anton Dubrovskiy, Houston, TX (US); Arcadius V. Krivoshein, Houston, TX (US)

(73) Assignee: UNIVERSITY OF HOUSTON SYSTEM, Houston, TX (US)

( * ) Notice: Subject to any disclaimer, the term of this patent is extended or adjusted under 35 U.S.C. 154(b) by 0 days.

(21) Appl. No.: 18/462,920

(22) Filed: Sep. 7, 2023

(65) Prior Publication Data

US 2023/0414566 A1    Dec. 28, 2023

Related U.S. Application Data

(63) Continuation of application No. 16/763,738, filed as application No. PCT/US2018/061414 on Nov. 16, 2018, now Pat. No. 11,806,333.

(60) Provisional application No. 62/587,151, filed on Nov. 16, 2017.

(51) Int. Cl.
*A61K 31/4015*    (2006.01)
*A61P 25/08*    (2006.01)
*A61K 31/165*    (2006.01)

(52) U.S. Cl.
CPC .......... *A61K 31/4015* (2013.01); *A61P 25/08* (2018.01); *A61K 31/165* (2013.01)

(58) Field of Classification Search
CPC .... A61K 31/165; A61K 31/4015; A61P 25/08
See application file for complete search history.

(56) References Cited

U.S. PATENT DOCUMENTS 6,200,993 B1 * 3/2001 Cote ...................... A61P 27/02
546/264

* cited by examiner

*Primary Examiner* — Marcos L Sznaidman
(74) *Attorney, Agent, or Firm* — Jackson Walker LLP (57) ABSTRACT

Aryl-substituted acetamide and pyrrolidin-2-one (γ-butyrolactam) derivatives have useful activity in the inhibition, prevention, or treatment of seizures. The derivatives may be useful in the treatment of epilepsy, including medically refractory epilepsy, and nerve agent poisoning.

2 Claims, 9 Drawing Sheets

FIG. 1
PRIOR ART imidazolidine-2,4-diones (hydantoins)

N-carbamoylacetamides (acetylureas)

pyrrolidine-2,5-diones (succinimides)

pyrrolidin-2-ones (γ-butyrolactams)

acetamides

Activity of racemic 3-ethyl-3-phenylpyrrolidin-2-one in preventing convulsions in animal models of medically refractory epilepsy

| Model of medically refractory epilepsy | $ED_{50}$, mg / kg of body weight |
|---|---|
| | (the 95% confidence interval is shown in parentheses) |
| 6 Hz (44 mA) seizures (mice, i.p.) | 48 (42-54) |
| 6 Hz (44 mA) seizures (mice, p.o.) | 84 (68-106) |
| Corneal kindling seizures (mice, i.p.) | 29 (22-37) |
| Mesial temporal lobe epilepsy (MTLE) model (mouse brain slices) | 30% suppression of HPDs at 50 mg/kg of body weight and 83% suppression of HPDs at 100 mg/kg of body weight |

ARYL-SUBSTITUTED ACETAMIDE AND PYRROLIDIN-2-ONE DERIVATIVES AND THEIR USE FOR THE TREATMENT OF SEIZURES

This application is a continuation of and claims priority to U.S. patent application Ser. No. 16/763,738, filed May 13, 2020, entitled "Aryl-Substituted Acetamide and Pyrrolidin-2-one Derivatives and Their Use for the Treatment of Seizures," which is a 371 application of PCT/US2018/061414, filed Nov. 16, 2018, which claims priority to U.S. Provisional Patent Application No. 62/587,151, filed Nov. 16, 2017, entitled "Aryl-Substituted Acetamide and Pyrrolidin-2-one Derivatives and Their Use for the Treatment of Seizures," the entire contents of which are hereby incorporated by reference.

BACKGROUND

This disclosure pertains to aryl-substituted acetamide and pyrrolidin-2-one (γ-butyrolactam) derivatives having useful anti-seizure activity as applicable to epilepsy and nerve agent poisoning.

Epilepsy affects about 70 million people worldwide and thus is the most common type of neurological disorder. Epileptic seizures result from the imbalance between the excitatory and inhibitory processes in the brain. Multiple proteins contribute to these processes, with the $GABA_A$ receptors, NMDA receptors, and $Na^+$ channels being regarded as the most important. Despite many available antiepileptic drugs (AEDs), the pharmacotherapy of epilepsy remains to be hampered by two major issues. One issue is drug resistance (medically refractory epilepsy), when the current first-line AEDs cannot control seizures in 25-41% of patients. The second issue are side effects that limit the usage of some effective AEDs. For example, AEDs that act primarily through the potentiation of the $GABA_A$ receptor function frequently produce sedation or dizziness and result in physical dependency (addiction). Seizures similar to epileptic ones are produced by chemical warfare nerve agents (such as Soman). Therefore, any treatments for epileptic seizures will also be of value in treatment and prevention of nerve agent poisoning.

Figure 1:
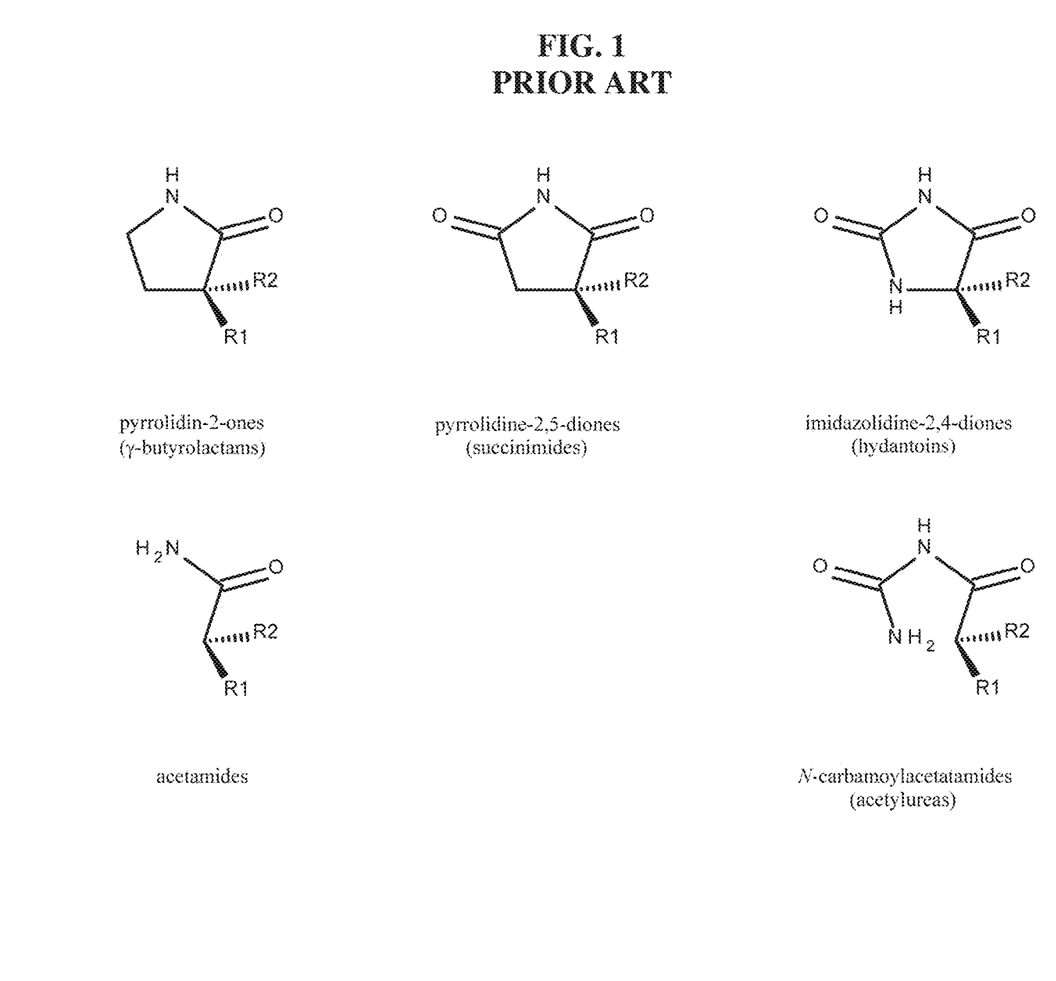
FIG. 1 shows previously reported anticonvulsant α-substituted acetamides, lactams, cyclic imides, and structurally related compounds.

The antiepileptic activity of α-substituted acetamides and lactams has been known for over six decades. The structural similarity of anticonvulsant acetamides, lactams, cyclic imides, acylureas, hydantoins, and barbiturates and the consequent implication of a shared mechanism of action and protein target has been fully realized only very recently. This realization triggered extensive studies (Krivoshein, 2016a) that proposed the neuronal nicotinic acetylcholine receptors (nAChRs) in the brain as the shared targets of anticonvulsant α-substituted acetamides, lactams, and cyclic imides. FIG. 1 shows anticonvulsant α-substituted acetamides, lactams, cyclic imides, and structurally related compounds. In the upper row are cyclic compounds and in the lower row are the corresponding acyclic compounds (Krivoshein, 2016b).

Some aryl-containing acetamide and lactam derivatives have been reported, including those with the structures shown below.

Azetidin-2-Ones:

Reported compounds include 3,3-disubstituted azetidin-2-ones, derivatives with $R_1$=Ph (phenyl), $R_1$=Ph with ethoxy, alkyl, phenyl, and chloro substitution, $R_2$=methyl, ethyl, other alkyl, or phenyl, as well as several N-alkyl derivatives (Testa et al., 1963; Fontanella, et al., 1973).

Pyrrolidin-2-Ones:

Reported compounds include several 3- and 5-arylpyrrolidin-2-ones, including some N-alkyl substituted ones (Bavin, 1996; Bocchi et al., 1971; Marshall, 1958; Testa et al., 1966; Bertozzi et al., 1996; Brine et al., 1983).

Aryl-Substituted Acetamides:

Reported compounds include substitution around the benzene ring in phenylacetamide and N-unsubstituted and N-substituted amides (Easterly et al., 1954; Kitamura et al., 2013; Clark et al., 1987; Shindikar et al., 2006). Reported compounds also include α-substituted phenylacetamides ($R_2$=H), where $R_1$=methyl (Me), ethyl (Et), including N-alkyl and N-aryl derivatives. Reported compounds also include unsubstituted ($R_1$=$R_2$=H) and α-substituted ($R_1$=Et, Ph; $R_2$=H) derivatives with various substituents around the benzene ring (hydroxy, amino, chloro, bromo, nitro, alkyl, alkoxy). Additional reported compounds include disubstituted phenylacetamides where $R_1$=$R_2$=Me, and derivatives with various substitution around the benzene ring (chloro, methyl, methoxy). (Pettersson, 1956; Chapman et al., 1957; Kitamura et al., 2013; Volwiler et al., 1936; Mijin et al., 2000; Roufos et al., 1996; Canonica et al., 1958; Koltunov et al., 2004).

Homologous Acetamides:

Reported compounds include those where $R_1$=$R_2$=H or Me, n=1: (additional alkyl and aryl substitution, including chlorophenyl), and where $R_1$=Me, $R_2$=Et, n=1, and where $R_1$=ethyl, or other alkyl, $R_2$=H, n=1 to 6, and also N-alkyl and N,N-dialkyl derivatives. (Kushner et al., 1951; Koltunov et al., 2004; Chapman et al., 1957; Blicke et al., 1938).

Phenylacetamide with α-Fluoro Substitution, and its N-Methyl-N-Phenyl Derivatives (Cavalleri et al., 1968):

Hydroxy-Containing Derivatives of Acetamide:

Reported compounds include those where n=0, 1, or 2, R=Me, CF$_3$, C$_7$H$_{15}$, Et, including those with various substitution around the benzene ring (methyl, alkyl, alkoxy, chloro, fluoro, trifluoromethyl), and including 3,4-dichlorophenyl derivative, p-bromophenyl, p-fluoro, and p-chloro derivatives. (Choudhury-Mukherjee et al., 2003; Schenck et al., 2004; Lenkowski et al., 2004; Meza-Toledo et al., 2008a; Joseph-Nathan et al., 1978; Meza-Toledo et al., 2004; Sandoval et al., 1995; Meza-Toledo et al., 2008b; Meza-Toledo et al., 1990; Meza-Toledo et al., 1995; Meza-Toledo et al., 1998; Carvajal-Sandoval et al., 1998).

While some of these derivatives are known to have anticonvulsant activity, none were reported to inhibit neuronal nicotinic acetylcholine receptors (nAChRs) or be effective in medically refractory epilepsy.

SUMMARY

The present disclosure pertains to orally available aryl-substituted acetamide and pyrrolidin-2-one derivatives that are effective in treating medically refractory epilepsy and nerve agent poisoning.

Tests of various α-substituted acetamides, lactams, and cyclic imides in rodent models of conventional as well as medically refractory epilepsy suggested that the α-phenyl-substituted acetamide and lactam derivatives exhibit a better spectrum of antiepileptic activity than the corresponding cyclic imide derivatives. Specifically, the α-phenyl-substituted acetamide and lactam derivatives show a broader activity in the models of medically refractory epilepsy.

The present derivatives are distinct from those previously reported or utilized for several reasons. First, they have electronegative substituents (F, Cl, I, Br, CF$_3$, CCl$_3$, methoxy, methoxy-ethoxy) in the phenyl ring that prevent undesirable metabolic reactions (such as p-hydroxylation) and improve potency and biodistribution. They also lack a hydroxy group in the α-position, which prevents undesirable metabolic reactions (thus producing compounds with better safety margin) and excessive hydrogen bonding (improving solubility). The achiral nature of 2-methyl-2-phenylpropanamide derivatives is also expected to simplify manufacturing (including quality control), preclinical and clinical testing, and therapeutic monitoring in a clinical setting. Unlike many other compounds, the proposed derivatives have robust activity in rodent models of medically refractory (drug-resistant) epilepsy and thus are well positioned to fill the unmet need of treating medically refractory epilepsy (which accounts for up to a third of all epilepsy cases). Finally, the derivatives show good oral bioavailability (which is highly beneficial, since antiepileptic drugs (AEDs) are typically administered orally).

DETAILED DESCRIPTION OF PREFERRED EMBODIMENTS

The present disclosure relates to aryl-substituted acetamide and pyrrolidin-2-one (γ-butyrolactam) derivatives endowed with anti-seizure activity.

Those skilled in the art will appreciate that some substituents introduced in the aromatic ring may have a profound influence on pharmacological potency and ADME of drugs. For example, the introduction of a stable substituent in the para position may prevent metabolic elimination due to enzymatic para-hydroxylation and thus give a derivative with a longer duration of action. In some instances, the same can be accomplished via the introduction of a stable substituent in the meta position, in which case para-hydroxylation is prevented due to sterical hindrance (mismatch between the molecular structure of the substituted aromatic ring and the active site of the hydroxylase).

Preferred embodiments include 2-methyl-2-phenylpropanamide, 2-phenylbutyramide, and 2-phenylpropanamide derivatives bearing single or multiple substituents on the aromatic ring and having the formula shown below:

where $R_1$ and $R_2$ are each independently selected from the group consisting of hydrogen, methyl ($CH_3$), trifluoromethyl ($CF_3$), 2,2,2-trifluoroethyl ($CH_2CF_3$), and ethyl ($CH_2CH_3$), and $R_3$-$R_7$ are each independently selected from the group consisting of H, F, Cl, Br, I, $CF_3$, $CCl_3$, $CBr_3$, $OCH_3$, $OCH_2CH_2OCH_3$, CN, and including any pharmaceutically acceptable salts, co-crystals, or prodrugs thereof.

Additional preferred embodiments include 4-phenylbutyramide derivatives bearing single or multiple substituents in the aromatic ring and having the formula shown below:

where $R_3$-$R_7$ are each independently selected from the group consisting of H, F, Cl, Br, I, $CF_3$, $CCl_3$, $CBr_3$, $OCH_3$, $OCH_2CH_2OCH_3$, CN, and including any pharmaceutically acceptable salts, co-crystals, or prodrugs thereof.

Additional preferred embodiments include 1-phenylcyclopropane-1-carboxamide derivatives bearing single or multiple substituents in the aromatic ring and having the formula shown below:

where $R_1$-$R_5$ are each independently selected from the group consisting of H, F, Cl, Br, I, $CF_3$, $CCl_3$, $CBr_3$, $OCH_3$, $OCH_2CH_2OCH_3$, CN, and including any pharmaceutically acceptable salts, co-crystals, or prodrugs thereof.

Additional preferred embodiments include pyrrolidin-2-one (γ-butyrolactam) derivatives bearing single or multiple substituents in the aromatic ring and having the formula shown below:

where $R_2$ is selected from the group consisting of H, methyl ($CH_3$), trifluoromethyl ($CF_3$), 2,2,2-trifluoroethyl ($CH_2CF_3$), and ethyl ($CH_2CH_3$), and $R_3$-$R_7$ are each independently selected from the group consisting of H, F, Cl, Br, I, $CF_3$, $CCl_3$, $CBr_3$, $OCH_3$, $OCH_2CH_2OCH_3$, CN, and including any pharmaceutically acceptable salts, co-crystals, or prodrugs thereof.

The present compounds set forth above, alone or in a combination with appropriate carriers/excipients, are useful in preventing, inhibiting, or alleviating convulsive and non-convulsive seizures, such as those encountered in epilepsy (including, but not limited to, medically refractory epilepsy) and in nerve agent (including but not limited to organophosphorus compounds, such as soman, etc.) poisoning.

The exemplary compounds described herein may occur in different geometric and enantiomeric forms, and both pure forms and mixtures of these separate isomers are included in the scope of this invention, as well as any physiologically functional or pharmacologically acceptable salts, co-crystals, or prodrugs thereof. Production of these alternate forms would be well within the capabilities of one skilled in the art.

The current invention also pertains to methods of prevention or seizures or treatment of epilepsy or treatment of individuals suffering from seizures, including the step of administering a compound in accordance with preferred embodiments disclosed herein.

In another aspect of the present invention there is provided a pharmaceutical composition including a therapeutically effective amount of a compound that prevents or treats seizures as discussed above and a pharmaceutically acceptable excipient, adjuvant, carrier, buffer or stabilizer. A "therapeutically effective amount" is to be understood as an amount of an exemplary compound that is sufficient to show inhibitory effects on seizures. The actual amount, rate and time-course of administration will depend on the nature and severity of the disease or condition being treated. Prescription of treatment is within the responsibility of general practitioners and other medical doctors. The pharmaceutically acceptable excipient, adjuvant, carrier, buffer or stabiliser should be non-toxic and should not interfere with the efficacy of the active ingredient. The precise nature of the carrier or other material will depend on the route of administration, which may be oral (which is preferred), or by injection, such as cutaneous, subcutaneous, or intravenous injection, or by microneedle delivery, or by patch delivery, or by dry powder inhaler.

Pharmaceutical compositions for oral administration may be in tablet, capsule, powder or liquid form. A tablet may comprise a solid carrier or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included. A capsule may comprise a solid carrier such as gelatin. For intravenous, cutaneous or subcutaneous injection, the active ingredient will be in the form of a parenterally acceptable aqueous solution which is pyrogen-free and has a suitable pH, isotonicity and stability. Those of relevant skill in the art are well able to prepare suitable solutions using, for example, isotonic vehicles such as sodium chloride solution, Ringer's solution, or lactated Ringer's solution. Preservatives, stabilizers, buffers, antioxidants and/or other additives may be included as required.

In another aspect, there is provided the use in the manufacture of a medicament of a therapeutically effective amount of an anti-seizure or anti-epileptic compound as defined above for administration to a subject.

The terms "anti-seizure" or "anti-epileptic" as used herein refer to the inhibition, prevention, or treatment of seizures or epilepsy, including medically refractory epileptic seizures or seizures caused by nerve agent poisoning.

The term "pharmaceutically acceptable salt" used throughout the specification is to be taken as meaning any acid or base derived salt formed from hydrochloric, sulfuric, phosphoric, acetic, citric, oxalic, malonic, salicylic, malic, fumaric, succinic, ascorbic, maleic, methanesulfonic, isoethonic acids and the like, and potassium carbonate, sodium or potassium hydroxide, ammonia, triethylamine, triethanolamine and the like.

The term "co-crystal" used throughout the specification means a solid, crystalline material that includes a drug or a pharmacological substance in the same crystal lattice as an acceptable excipient or other typically inactive ingredient. (FDA Guidance for Industry—Regulatory Classification of Pharmaceutical Co-Crystals, April 2013).

The term "prodrug" means a pharmacological substance that is administered in an inactive, or significantly less active, form. Once administered, the prodrug is metabolised in vivo into an active metabolite.

The term "therapeutically effective amount" means a nontoxic but sufficient amount of the drug to provide the desired therapeutic effect. The amount that is "effective" will vary from subject to subject, depending on the age and general condition of the individual, the particular concentration and composition being administered, and the like. Thus, it is not always possible to specify an exact effective amount. However, an appropriate effective amount in any individual case may be determined by one of ordinary skill in the art using routine experimentation. Furthermore, the effective amount is the concentration that is within a range sufficient to permit ready application of the formulation so as to deliver an amount of the drug that is within a therapeutically effective range.

Further aspects of the present invention will become apparent from the following description given by way of example only and with reference to the accompanying synthetic schemes.

Figure 2:
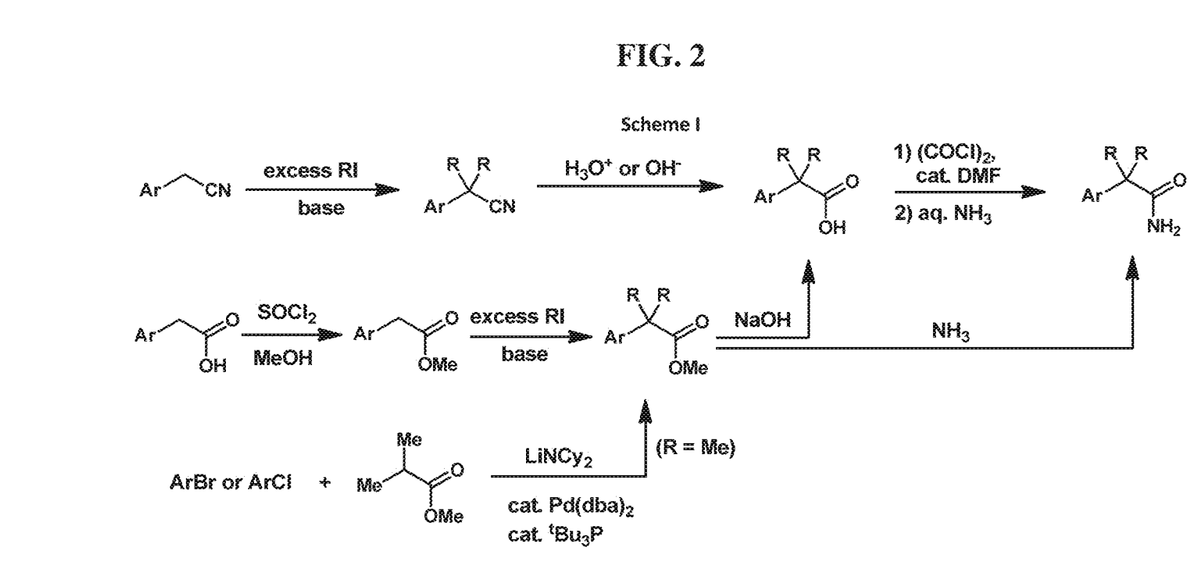
FIG. 2 shows Scheme I, a representative synthetic scheme for exemplary compounds having anti-seizure activity in accordance with preferred embodiments described herein.

There are multiple approaches suitable for the preparation of compounds having the formulas set forth above. FIG. 2 shows Scheme I, or an exemplary synthetic scheme for certain compounds in accordance with preferred embodiments herein. In Scheme I, target amides can be easily prepared from the corresponding acids through addition of the intermediate acid chloride to an aqueous solution of ammonia. Some of such acids are available via acid- or base-catalyzed hydrolysis of the corresponding nitriles or methyl esters. If R is an alkyl substituent, such as methyl or ethyl, both the nitrile and the methyl ester are accessible through extensive alkylation of the corresponding unsubstituted substrates in presence of an alkylating agent, such as methyl or ethyl iodide, and a base, such as NaH (Takamatsu et al., 2015). Methyl esters can be prepared from the reaction of corresponding acids with thionyl chloride in methanol. Many of starting nitriles and acids are commercially available at low cost, with diverse substitution patterns: fluoro-substituted (including several fluorine atoms, symmetrical and unsymmetrical patterns), trifluoromethyl-substituted, methoxy-, bromo-, and iodo-derivatives, amongst others. Both pathways consist of only a few synthetic steps, and are deemed to be scalable. Some methyl esters are known to be converted directly into primary amides via a transamination procedure (Bundesmann et al., 2010; Gust et al., 1987). Some gem-dimethyl esters can be alternatively assembled via Pd-catalyzed α-arylation procedure, reported by Hartwig (Jorgensen et al., 2002; Hama et al., 2008), that allows connection of the aryl and aliphatic portion of the target amides. In such cases, commercially available aryl bromides or chlorides can be used as starting materials, to be coupled with methyl isobutyrate.

Figure 3:
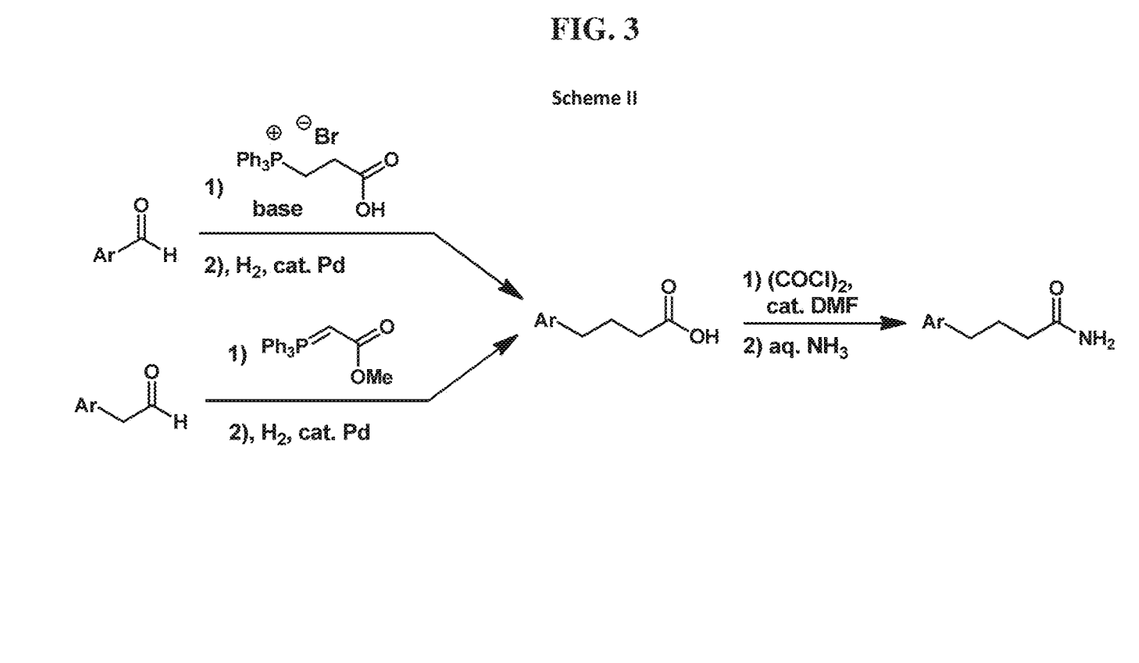
FIG. 3 shows Scheme II, a representative synthetic scheme for exemplary compounds having anti-seizure activity in accordance with preferred embodiments described herein.

FIG. 3 shows Scheme II, an exemplary synthetic scheme for certain compounds in accordance with preferred embodiments herein. In Scheme II, target amides can be prepared from the corresponding acids through addition of the intermediate acid chloride to an aqueous solution of ammonia. Such acids can be prepared from the Wittig reaction of substituted benzaldehydes with ylide derived from 3-(triphenylphosphonium)propionic acid bromide (Zhang, X. et al., 2016), or of their homologues with (carbethoxymethylene) triphenylphosphorane (Wang et al., 2001), followed by hydrogenation of the resulting double bond in either case. While many substituted benzaldehydes are commercially available, arylacetaldehydes can be easily prepared from the corresponding esters via reduction/oxidation (for example, LAH followed by Dess-Martin oxidation) sequence (Kolonko et al., 2008).

Figure 4:
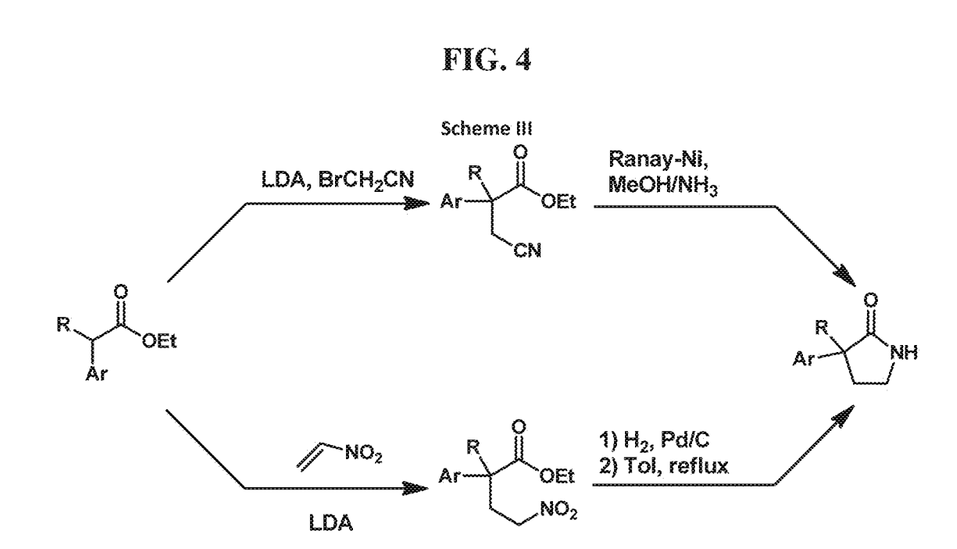
FIG. 4 shows Scheme III, a representative synthetic scheme for exemplary compounds having anti-seizure activity in accordance with preferred embodiments described herein.

FIG. 4 shows Scheme III, an exemplary synthetic scheme for certain compounds in accordance with preferred embodiments herein. In Scheme III, target lactams can be prepared from aryl acetic esters: α-methyl or α-ethyl substituted, or unsubstituted. Their deprotonation with lithium diisopropylamide, followed by addition of commercially available bromo- or chloroacetonitrile, can install the necessary two-carbon fragment (WO2007/127763). The nitrile can be reduced to an amino group by reported procedure and following cyclization in situ should yield the desired lactams (Doherty et al., 2012; Reddy et al., 1996). Alternatively, the two carbon-fragment can be installed via Michael addition of nitroethylene to the starting ester (Flintoft et al., 1999), and the reduction (Nilsson et al., 1992; Bousquet et al., 2015) of the nitro group followed by lactamization in situ should provide the desired target substrates. The starting materials, esters, can be prepared via classic malonic ester synthesis or by monoalkylation of the corresponding aryl acetic esters (Kato et al., 2003).

Figure 5:
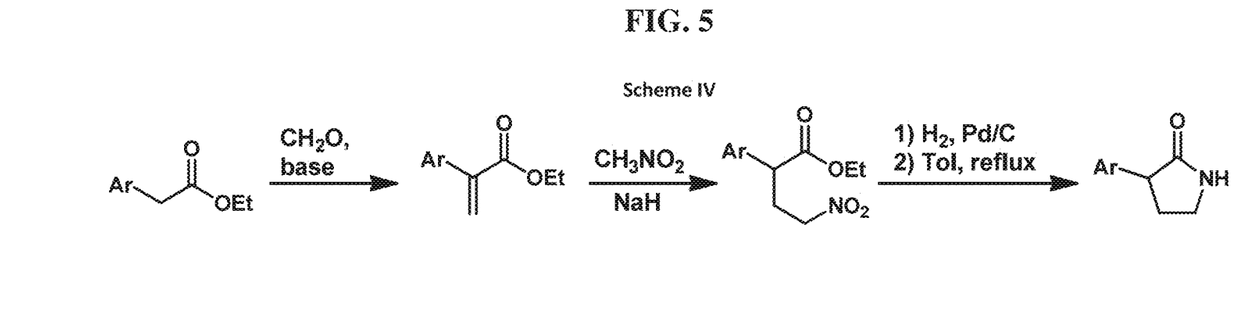
FIG. 5 shows Scheme IV, a representative synthetic scheme for exemplary compounds having anti-seizure activity in accordance with preferred embodiments described herein.

Additionally, unalkylated aryl-lactams can be prepared by Michael addition of nitromethane to alkenyl esters (Yin et al., 2015; Jiang et al., 2012), followed by reduction of the nitro group and lactamization (Scheme IV), as shown in Scheme IV in FIG. 5. Alkenyl esters can be prepared via aldol condensation of aryl acetic esters with formaldehyde (Zhu et al., 2017).

EXAMPLE 1. SYNTHESIS

Figure 6:
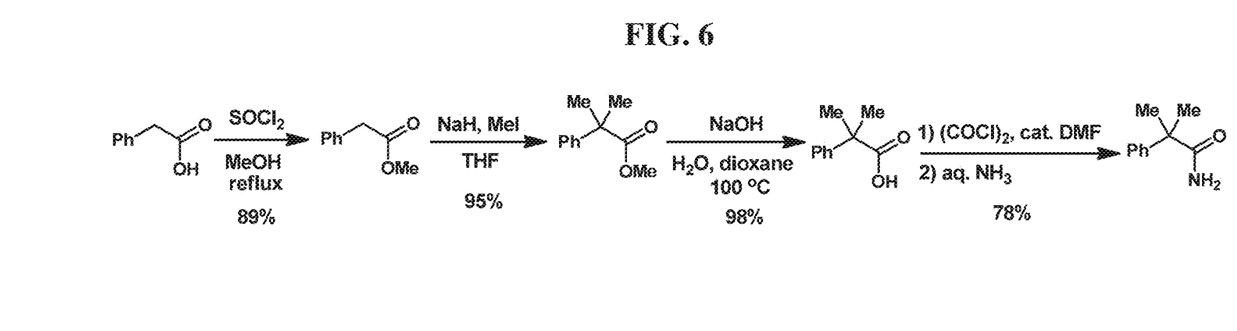
FIG. 6 shows a synthetic scheme for the preparation of 2-methyl-2-phenylpropanamide, in accordance with preferred embodiments described herein

FIG. 6 shows a synthetic scheme for the preparation of 2-methyl-2-phenylpropanamide.

Methyl ester formation. Thionyl chloride, 10.60 mL (2.0 equiv, 0.146 mol), was added dropwise to a mixture of 10.00 g of phenylacetic acid (73.4 mmol) in 40 mL methanol at 0° C. After 10 min of stirring, the mixture was brought to a reflux. Upon completion of the reaction (5 h, control by TLC), the reaction mixture was cooled to room temperature and concentrated to ~15 mL. The mixture was transferred to 40 mL of saturated $NaHCO_3$ solution and extracted with dichloromethane (3×20 mL). Combined organic fractions were washed with brine (30 mL), filtered through cotton and concentrated under reduced pressure to yield 9.84 g (65.5 mmol) of a methyl 2-phenylacetate, clear liquid (89%).

Dimethylation. A solution of methyl 2-phenylacetate (2.01 g, 13.4 mmol) and methyl iodide (2.08 mL, 33.5 mmol, 2.5 equiv) in anhydrous THF (15 mL) was treated portionwise with sodium hydride (60% suspension in mineral oil, 1.18 g, 29.5 mmol, 2.2 equiv) at 0° C., warmed to room temperature and reacted for 24 h. The reaction mixture was transferred into a separatory funnel with ice/water and acidified with 1.0 M HCl (30 mL). The product was extracted with ethyl acetate (3×30 mL). The combined organic layers were washed brine (30 mL), filtered through cotton, and concentrated under reduced pressure to yield dark oil which was purified by flash chromatography (hexanes/ethyl acetate) to provide 2.26 g of methyl 2-methyl-2-phenylpropanoate, yellow oil (12.7 mmol, 95%).

Ester hydrolysis. Methyl 2-methyl-2-phenylpropanoate (0.840 g, 4.71 mmol) was dissolved in 5 mL of 1,4-dioxane and 10 mL of 1.0 M NaOH (10.0 mmol, 2.1 equiv) was added. The mixture was heated at 95° C. for 24 h. 20 mL of 1.0 M HCl was added and the mixture was extracted with dichloromethane (3×20 mL). Combined organic fractions were washed with brine (30 mL), filtered through cotton and concentrated under reduced pressure to yield a crude mixture which was purified by flash chromatography (hexanes/ethyl acetate), 0.758 g of 2-methyl-2-phenylpropanoic acid (4.62 mmol, 98%).

Amide formation. 1.26 mL of oxalyl chloride (14.70 mmol, 3.2 equiv) was added dropwise to the solution of 0.750 g (4.57 mmol) of 2-methyl-2-phenylpropanoic acid in 10 mL dichloromethane at 0° C. This was followed by the addition of 1 drop of DMF. The reaction mixture was brought to room temperature, and after 9 hours of stirring was slowly added to 20 mL of 30% aqueous $NH_3$ solution upon vigorous stirring. The stirring continued for 9 more hours. The reaction mixture diluted with water (20 mL), filtered from white precipitate into a separatory funnel, and washed with dichloromethane (3×30 mL). Combined organic fractions were washed with brine (30 mL), filtered through cotton and concentrated under reduced pressure to yield a crude amide, which was purified by flash chromatography (hexanes/ethyl acetate), 0.588 g of 2-methyl-2-phenylpropanamide (3.60 mmol, 78% yield). Melting point: 162.0° C.

Figure 7:
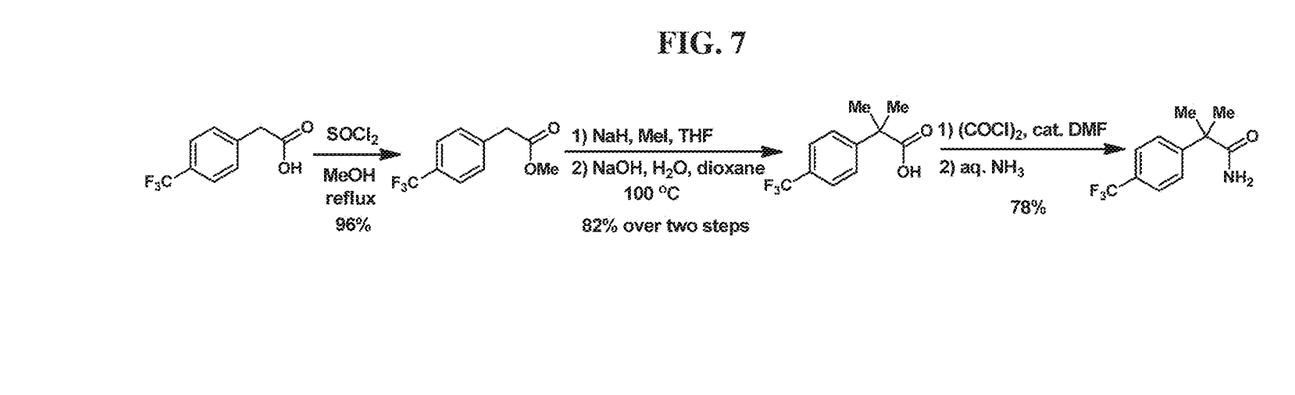
FIG. 7 shows a synthetic scheme for the preparation of 2-methyl-2-(4-(trifluoromethyl)phenyl)propanamide, in accordance with preferred embodiments described herein.

FIG. 7 shows a synthetic scheme for the preparation of 2-methyl-2-(4-(trifluoromethyl)phenyl)propanamide.

Methyl Ester formation. Thionyl chloride, 3.48 mL (2.0 equiv, 48.0 mmol), was added dropwise to a mixture of 4.96 g (24.3 mmol) of 2-(4-(trifluoromethyl)phenyl)acetic acid in 40 mL methanol at 0° C. After 10 min of stirring, the mixture was brought to a reflux. Upon completion of the reaction (8 h, control by TLC), the reaction mixture was cooled to room temperature and concentrated to ~10 mL. The mixture was transferred to 40 mL of saturated $NaHCO_3$ solution and extracted with dichloromethane (3×20 mL). Combined organic fractions were washed with brine (30 mL), filtered through cotton and concentrated under reduced pressure to yield 5.09 g (23.3 mmol) of methyl 2-(4-(trifluoromethyl) phenyl)acetate, clear liquid (96%).

Dimethylation and hydrolysis. A solution of methyl 2-(4-(trifluoromethyl)phenyl)acetate (5.09 g, 23.3 mmol) and methyl iodide (3.79 mL, 60.9 mmol, 2.6 equiv) in anhydrous THF (25 mL) was treated portionwise with sodium hydride (60% suspension in mineral oil, 2.15 g, 53.8 mmol, 2.3 equiv) at 0° C., warmed to room temperature and reacted for 24 h. The reaction mixture was transferred into a separatory funnel with ice/water and acidified with 1.0 M HCl (30 mL). The product was extracted with ethyl acetate (3×30 mL). The combined organic layers were washed brine, filtered through cotton, and concentrated under reduced pressure to yield dark oil. Unpurified dimethylated product was dissolved in 16 mL of 1,4-dioxane and 8 mL of 6.0 M NaOH (48.0 mmol, 2.1 equiv) was added. The mixture was heated at 95° C. for 24 h. 30 mL of 3.0 M HCl was added and the mixture was extracted with dichloromethane (3×20 mL). Combined organic fractions were washed with brine (30 mL), filtered through cotton and concentrated under reduced pressure to yield a crude mixture which was purified by flash chromatography (hexanes/ethyl acetate), 4.42 g of 2-methyl-2-(4-(trifluoromethyl)phenyl)propanoic acid (19.0 mmol, 82% over two steps).

Amide formation. 3.00 mL of oxalyl chloride (35.0 mmol, 2.0 equiv) was added dropwise to the solution of 4.021 g (17.3 mmol) of 2-methyl-2-(4-(trifluoromethyl)phenyl)propanoic acid in 35 mL dichloromethane at 0° C. This was followed by the addition of 2 drops of DMF. The reaction mixture was brought to room temperature, and after 9 hours of stirring was slowly added to 60 mL of chilled 30% aqueous $NH_3$ solution upon vigorous stirring. The stirring continued for 9 more hours. The reaction mixture was diluted with water (30 mL), filtered from white precipitate into a separatory funnel, and washed with dichloromethane (3×30 mL). Combined organic fractions were washed with brine (20 mL), filtered through cotton and concentrated under reduced pressure to yield a crude amide, 3.950 g. 2-Methyl-2-(4-(trifluoromethyl)phenyl)propanamide was recrystallized from anhydrous ethanol. White crystals, 3.133 g (78%). Melting point: 143.9° C.

Figure 8:
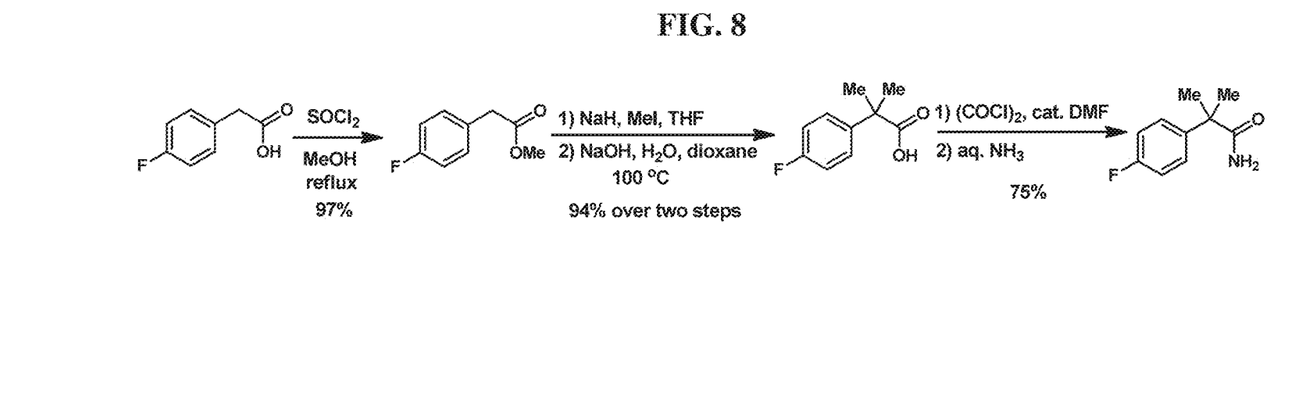
FIG. 8 shows a synthetic scheme for the preparation of 2-methyl-2-(4-fluorophenyl)propanamide, in accordance with preferred embodiments described herein.

FIG. 8 shows a synthetic scheme for the preparation of methyl-2-(4-fluorophenyl)propanamide.

Methyl ester formation. Thionyl chloride, 4.70 mL (2.0 equiv, 64.8 mmol), was added dropwise to a mixture of 5.01 g (32.5 mmol) of 2-(4-fluorophenyl)acetic acid in 40 mL methanol at 0° C. After 10 min of stirring, the mixture was brought to a reflux. Upon completion of the reaction (8 h, control by TLC), the reaction mixture was cooled to room temperature and concentrated to ~10 mL. Mixture was transferred to 40 mL of saturated $NaHCO_3$ solution and extracted with dichloromethane (3×20 mL). Combined organic fractions were washed with brine (30 mL), filtered through cotton and concentrated under reduced pressure to yield 5.28 g (31.4 mmol) of methyl 2-(4-fluorophenyl) acetate, clear liquid (97%).

Dimethylation and hydrolysis. A solution of methyl 2-(4-fluorophenyl)acetate (5.28 g, 31.4 mmol) and methyl iodide (4.89 mL, 78.5 mmol, 2.5 equiv) in anhydrous THF (25 mL) was treated portionwise with sodium hydride (60% suspension in mineral oil, 2.78 g, 69.5 mmol, 2.2 equiv) at 0° C., warmed to room temperature and reacted for 24 h. The reaction mixture was transferred into a separatory funnel with ice/water and acidified with 1.0 M HCl (30 mL). The product was extracted with ethyl acetate (3×30 mL). The combined organic layers were washed brine, filtered through cotton, and concentrated under reduced pressure to yield dark oil. Unpurified dimethylated product was dissolved in 15 mL of 1,4-dioxane and 14 mL of 6.0 M NaOH (84.0 mmol, 2.7 equiv) was added. The mixture was heated at 95° C. for 24 h. 40 mL of 3.0 M HCl was added and the mixture was extracted with dichloromethane (3×20 mL). Combined organic fractions were washed with brine (30 mL), filtered through cotton and concentrated under reduced pressure to yield a crude mixture which was purified by flash chromatography (hexanes/ethyl acetate), 5.36 g of 2-methyl-2-(4-fluorophenyl)propanoic acid (29.4 mmol, 94% over two steps).

Amide formation. 4.00 mL of oxalyl chloride (46.7 mmol, 1.6 equiv) was added dropwise to the solution of 5.329 g (29.2 mmol) of 2-methyl-2-(4-fluorophenyl)propanoic acid in 30 mL dichloromethane at 0° C. This was followed by the addition of 2 drops of DMF. The reaction mixture was brought to room temperature, and after 9 hours of stirring was slowly added to 60 mL of chilled 30% aqueous $NH_3$ solution upon vigorous stirring. The stirring continued for 9 more hours. The reaction mixture was diluted with water (30 mL), filtered from white precipitate into a separatory funnel, and washed with dichloromethane (3×30 mL). Combined organic fractions were washed with brine (20 mL), filtered through cotton and concentrated under reduced pressure to yield a crude amide, 5.365 g. 2-Methyl-2-(4-fluorophenyl)propanamide was recrystallized from anhydrous ethanol. White crystals, 3.993 g (75%). Melting point: 130.7° C.

Figure 9:
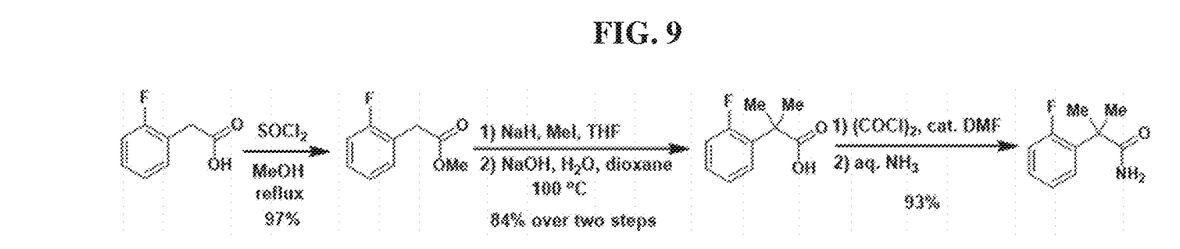
FIG. 9 shows a synthetic scheme for the preparation of 2-methyl-2-(2-fluorophenyl)propanamide, in accordance with preferred embodiments described herein.

FIG. 9 shows a synthetic scheme for the preparation of 2-methyl-2-(2-fluorophenyl)propanamide.

Methyl Ester formation. Thionyl chloride, 5.64 mL (2.0 equiv, 77.74 mmol), was added dropwise to a mixture of 5.990 g (38.87 mmol) of 2-(2-fluorophenyl)acetic acid in 40 mL methanol at 0° C. After 10 min of stirring, the mixture was brought to a reflux. Upon completion of the reaction (8 h, control by TLC), the reaction mixture was cooled to room temperature and concentrated to ~10 mL. The mixture was transferred to 40 mL of saturated $NaHCO_3$ solution and extracted with dichloromethane (3×20 mL). Combined organic fractions were washed with brine (30 mL), filtered through cotton and concentrated under reduced pressure to yield 6.373 g (37.89 mmol) of methyl 2-(2-fluorophenyl)acetate, clear liquid (97%).

Dimethylation and hydrolysis. A solution of methyl 2-(2-fluorophenyl)acetate (6.373 g, 37.89 mmol) and methyl iodide (5.90 mL, 94.8 mmol, 2.5 equiv) in anhydrous THF (25 mL) was treated portionwise with sodium hydride (60% suspension in mineral oil, 3.32 g, 83.0 mmol, 2.2 equiv) at 0° C., warmed to room temperature and reacted for 24 h. The reaction mixture was transferred into a separatory funnel with ice/water and acidified with 1.0 M HCl (30 mL). The product was extracted with ethyl acetate (3×30 mL). The combined organic layers were washed brine, filtered through cotton, and concentrated under reduced pressure to yield light yellow oil. The oil was dissolved in 16 mL of 1,4-dioxane and 19.0 mL of 6.0 M NaOH (113.7 mmol, 3.0 equiv) was added. The mixture was heated at 95° C. for 24 h. 30 mL of 3.0 M HCl was added and the mixture was extracted with dichloromethane (3×20 mL). Combined organic fractions were washed with brine (30 mL), filtered through cotton and concentrated under reduced pressure to yield a crude mixture which was purified by flash chromatography (hexanes/ethyl acetate), 5.799 g of 2-methyl-2-(2-fluorophenyl)propanoic acid (31.83 mmol, 84% over two steps).

Amide formation. 5.44 mL of oxalyl chloride (63.4 mmol, 2.0 equiv) was added dropwise to the solution of 5.776 g (31.70 mmol) of 2-methyl-2-(2-fluorophenyl)propanoic acid in 35 mL dichloromethane at 0° C. This was followed by the addition of 2 drops of DMF. The reaction mixture was brought to room temperature, and after 9 hours of stirring was slowly added to 60 mL of chilled 30% aqueous $NH_3$ solution upon vigorous stirring. The stirring continued for 9 more hours. The reaction mixture was diluted with water (30 mL), filtered from white precipitate into a separatory funnel, and washed with dichloromethane (3×30 mL). Combined organic fractions were washed with brine (20 mL), filtered through cotton and concentrated under reduced pressure to yield a crude amide. 2-Methyl-2-(2-fluorophenyl)propanamide was purified via column chromatography (hexanes/ethyl acetate) and additionally recrystallized from MeOH/water. White crystals, 5.342 g (29.48 mmol, 93%). Melting point: 95.9° C.

Figure 10:
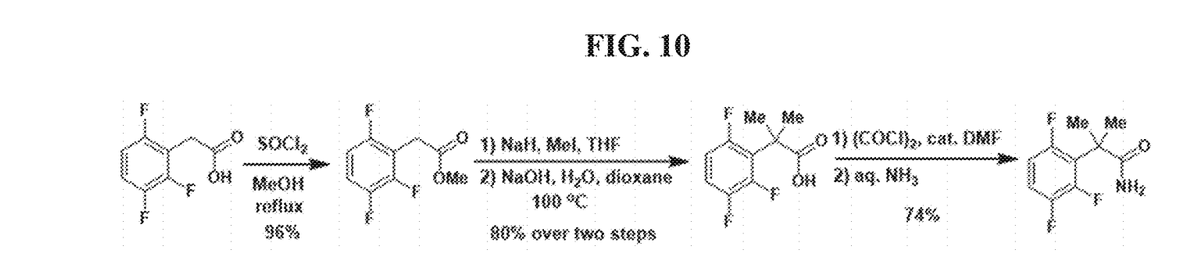
FIG. 10 shows a synthetic scheme for the preparation of 2-methyl-2-(2,3,6-trifluorophenyl)propanamide, in accordance with preferred embodiments described herein.

FIG. 10 shows a synthetic scheme for the preparation of 2-methyl-2-(2,3,6-trifluorophenyl)propanamide.

Methyl Ester formation. Thionyl chloride, 3.79 mL (2.0 equiv, 52.3 mmol), was added dropwise to a mixture of 4.970 g (26.15 mmol) of 2-(2,3,6-trifluorophenyl)acetic acid in 40 mL methanol at 0° C. After 10 min of stirring, the mixture was brought to a reflux. Upon completion of the reaction (8 h, control by TLC), the reaction mixture was cooled to room temperature and concentrated to ~10 mL. The mixture was transferred to 40 mL of saturated $NaHCO_3$ solution and extracted with dichloromethane (3×20 mL). Combined organic fractions were washed with brine (30 mL), filtered through cotton and concentrated under reduced pressure to yield 5.123 g (25.10 mmol) of methyl 2-(2,3,6-trifluorophenyl)acetate, clear liquid (96%).

Dimethylation and hydrolysis. A solution of methyl 2-(2,3,6-trifluorophenyl)acetate (5.091 g, 24.94 mmol) and methyl iodide (3.89 mL, 62.46 mmol, 2.5 equiv) in anhydrous THF (25 mL) was treated portionwise with sodium hydride (60% suspension in mineral oil, 2.20 g, 55.05 mmol, 2.2 equiv) at 0° C., warmed to room temperature and reacted for 24 h. The reaction mixture was transferred into a separatory funnel with ice/water and acidified with 1.0 M HCl (30 mL). The product was extracted with ethyl acetate (3×30 mL). The combined organic layers were washed brine, filtered through cotton, and concentrated under reduced pressure to yield light yellow oil. The oil was dissolved in 16 mL of 1,4-dioxane and 12.5 mL of 6.0 M NaOH (74.82 mmol, 3.0 equiv) was added. The mixture was heated at 95° C. for 24 h. 30 mL of 3.0 M HCl was added and the mixture was extracted with dichloromethane (3×20 mL). Combined organic fractions were washed with brine (30 mL), filtered through cotton and concentrated under reduced pressure to yield a crude mixture which was purified by flash chromatography (hexanes/ethyl acetate), 4.353 g of 2-methyl-2-(2,3,6-trifluorophenyl)propanoic acid (19.95 mmol, 80% over two steps).

Amide formation. 3.42 mL of oxalyl chloride (39.86 mmol, 2.0 equiv) was added dropwise to the solution of 4.348 g (19.93 mmol) of 2-methyl-2-(2,3,6-trifluorophenyl)propanoic acid in 35 mL dichloromethane at 0° C. This was followed by the addition of 2 drops of DMF. The reaction mixture was brought to room temperature, and after 9 hours of stirring was slowly added to 60 mL of chilled 30% aqueous $NH_3$ solution upon vigorous stirring. The stirring continued for 9 more hours. The reaction mixture was diluted with water (30 mL), filtered from white precipitate into a separatory funnel, and washed with dichloromethane (3×30 mL). Combined organic fractions were washed with brine (20 mL), filtered through cotton and concentrated under reduced pressure to yield a crude amide. 2-Methyl-2-(2,3,6-trifluorophenyl)propanamide was purified via silica column chromatography (hexanes/ethyl acetate) and additionally recrystallized from MeOH/water. White crystals, 3.203 g (14.75 mmol, 74%). Melting point: 104.6° C.

EXAMPLE 2. ACTIVITY

Anti-seizure activity of representative 2-methyl-2-phenylpropanamide (2 M2PPA) derivatives was investigated in mice. The testing protocol was specifically designed to find orally bioavailable compounds active against medically refractory epilepsy. Representative compounds that were tested had the formula shown below with the substitutions provided in FIG. 11.

In the representative compounds that were tested, $R_1$ and $R_2$ were Me. Any substituents not explicitly specified on the phenyl ring were H. For example, in FIG. 11, 2-F refers to the above structure where $R_3$ is F, $R_1$ is Me, $R_2$ is Me, and $R_4$, $R_5$, $R_6$, and $R_7$ are all H. Representative compounds included 2-methyl-2-phenylpropanamide, 2-methyl-2-(2-fluorophenyl)propanamide, 2-methyl-2-(3-fluorophenyl)propanamide, 2-methyl-2-(4-fluorophenyl)propanamide, 2-methyl-2-(2,3,6-trifluorophenyl)propanamide, 2-methyl-2-(2-trifluoromethylphenyl)propanamide, 2-methyl-2-(3-trifluoromethylphenyl)propanamide, and 2-methyl-2-(4-trifluoromethylphenyl)propanamide.

Figure 11:
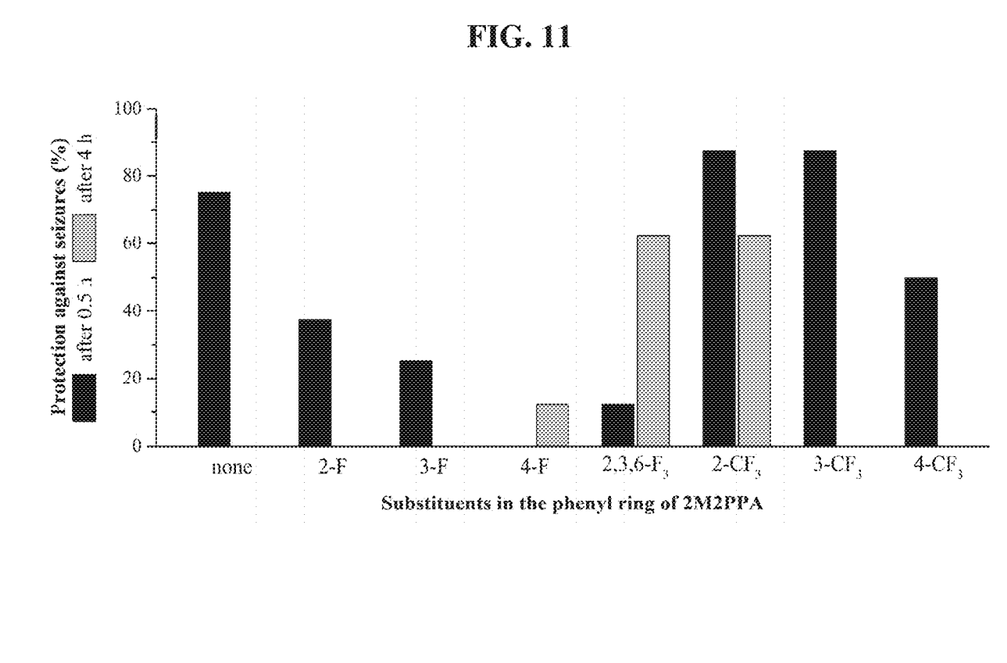
FIG. 11 shows anti-seizure activity of representative 2-methyl-2-phenylpropanamide (2 M2PPA) derivatives: 2-methyl-2-phenylpropanamide, 2-methyl-2-(2-fluorophenyl)propanamide, 2-methyl-2-(3-fluorophenyl)propanamide, 2-methyl-2-(4-fluorophenyl)propanamide, 2-methyl-2-(2,3,6-trifluorophenyl)propanamide, 2-methyl-2-(2-trifluoromethylphenyl)propanamide, 2-methyl-2-(3-trifluoromethylphenyl)propanamide, 2-methyl-2-(4-trifluoromethylphenyl)propanamide.

The derivatives identified in FIG. 11 were tested at the Epilepsy Therapy Screening Program, a component of the National Institute of Neurological Disorders and Stroke (NINDS), Rockville, MD, for their ability to protect mice against seizures produced by 6 Hz (44 mA) stimulation. The compounds suspended in PEG/Tween solution were administered orally to adult male C57BL/6 mice at a dose of 0.61 mmol/kg of body mass in a volume of 0.01 mL/g of body weight. The seizure challenge was performed either 0.5 h or 4 hours after administration. The animal studies were conducted in accordance with federal and State of Utah regulations using protocols approved by the University of Utah Institutional Animal Care and Use Committee (IACUC).

In the MES test (carried out as described by Krall et al., 1978), 50 mA current (60 Hz) was delivered for 2 s through corneal electrodes, and the animals were observed for the presence of tonic-clonic seizures. This test is a good model of motor (grand mal) seizures in humans.

In the 6 Hz (44 mA) test (carried out as described by Barton et al., 2001), 42 mA current (6 Hz) was delivered for 3 s through corneal electrodes, and the animals were observed for the presence of seizures. This test is a good model of medically refractory psychomotor seizures in humans.

Figure 12:
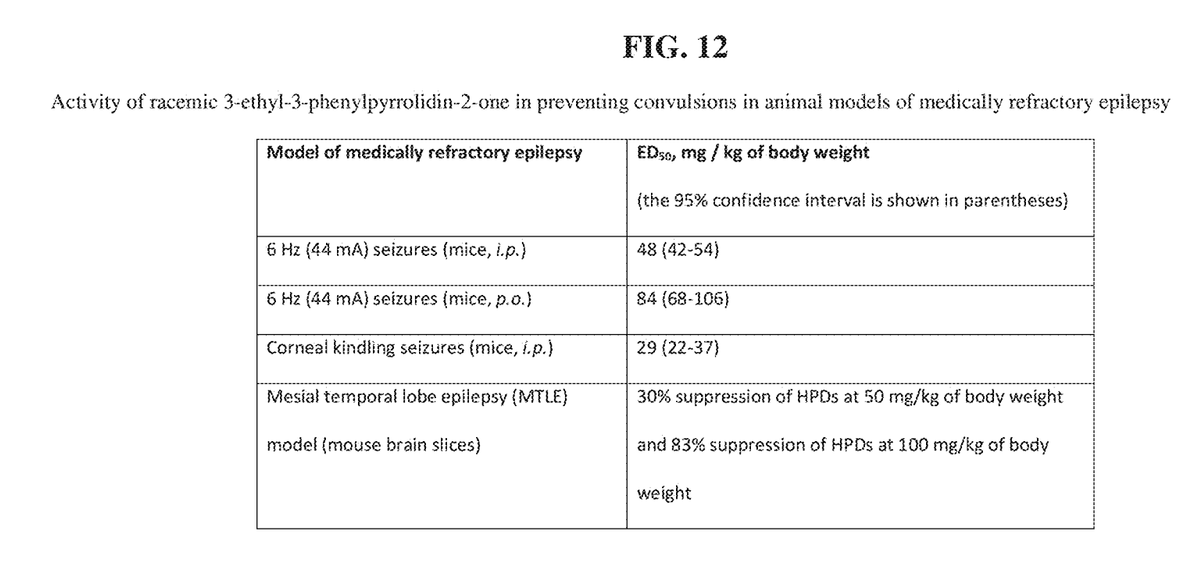
FIG. 12 shows activity of racemic 3-ethyl-3-phenylpyrrolidin-2-one in preventing convulsions in animal models of medically refractory epilepsy.

The results in FIG. 11 demonstrate that various representative 2-methyl-2-phenylpropanamide derivatives were effective in protecting mice from seizures upon oral administration. Additional results demonstrate that structurally similar compounds having the formulas identified above have similar activity. Indeed, data provided in FIG. 12 indicates that 3-ethyl-3-phenylpyrrolidin-2-one is active in multiple rodent models of medically refractory epilepsy.

REFERENCES

The following documents and publications are hereby incorporated by reference.

Barton, M. E., Klein, B. D., Wolf, H. H., White, H. S. (2001) Pharmacological characterization of the 6 Hz psychomotor seizure model in partial epilepsy. *Epilepsy Res.* 47, 217-227.

Bavin, P. M. G. (1966) (−)-5-Ethyl-5-phenyl-2-pyrrolidinone. Unusual reactions of 4-nitro-4-phenylhexanoic acid. *J. Med. Chem.* 9(1), 52-5.

Bertozzi, S., Salvadori, P. (1996) Synthesis of 3-phenyl- and 5-phenyl-2-pyrrolidinone via rhodium catalyzed carbonylation of allylamines, *Syn. Commun.* 26(16), 2959-65.

Blicke, F. F., Centolella, A. P. (1938) Acid amides as hypnotics. II. Acetamides, *J. Am. Chem. Soc.* 60, 2924-6.

Bocchi, V., Gardini, G. P., Pinza, M. (1971) Synthesis and activity of substituted 5-aryl-2-pyrrolidinones(DL), *Farmaco* 26(5), 429-34.

Bousquet, P. et al. (2015) Synthesis and biological evaluation of 2-aryliminopyrrolidines as selective ligands for I1 imidazoline receptors: discovery of new sympatho-inhibitory hypotensive agents with potential beneficial effects in metabolic syndrome. *J. Med. Chem.* 58(2): 878-87.

Brine, G. A., Boldt, K. G. (1983) Synthesis and anticonvulsant screening of 3,3-diphenyl-2-pyrrolidone derivatives. *J. Pharm. Sci.* 72(6), 700-2.

Bundesmann, M. W., Coffey, S. B.; Wright, S. W. (2010) Amidation of esters assisted by Mg(OCH$_3$)$_2$ or CaCl$_2$, *Tetrahedron Lett.* 51(30), 3879-82.

Canonica, L., Bonati, A., Tedeschi, C. (1958) Synthetic anticholesterolemic substances. I. Some derivatives of 2-phenylbutyric acid, *Farmaco* 13(4), 286-93.

Carvajal-Sandoval, G. et al. (1998) Synthesis and pharmacological evaluation of a new homologous series of (+/−)-p-fluoro-phenyl alcohol amide anticonvulsants, *Drug Res.* 48(4), 349-52.

Cavalleri, B.; Bellasio, E.; Gallo, G. G., Testa, E. (1968) Fluorinated organic compounds with potential biological activity. 3. Derivatives of alpha-fluorophenylacetic acid, *Farmaco* 23(12), 1127-40.

Chapman, M. V. A.; McCrea, P. A., Marshall, P. G., Sheahan, M. M. (1957) Derivatives of acetamide and benzamide as hypnotics, *J. Pharm. Pharmac.* 9, 20-8.

Choudhury-Mukherjee, I. et al. (2003) Design, synthesis, and evaluation of analogues of 3,3,3-trifluoro-2-hydroxy-2-phenyl-propionamide as orally available general anesthetics, *J. Med. Chem.* 46(12), 2494-501.

Clark, C. R., Davenport, T. W. (1987) Anticonvulsant activity of some 4-aminophenylacetamides, *J. Pharm. Sci.* 76(1), 18-20.

Doherty, G. A. et al. (2012) Discovery of diphenyl lactam derivatives as N-type calcium channel blockers. *Bioorg. Med. Chem. Lett.* 22(4), 1716-8.

Easterly, W. D., Larocca, J. P. (1954) The preparation of some amides of dichloro-acetaldehyde, *J. Am. Pharm. Assoc.* 43(1), 59-60.

Flintoft, R. J.; Buzby, J. C.; Tucker, J. A. (1999) Alkylation of ketone and ester lithium enolates with nitroethylene, *Tetrahedron Lett.* 40(24), 4485-8.

Fontanella, L., Pifferi, G., Testa, E. Consonni, P. (1973) Substances active on the C.N.S. L. Synthesis of 3-ethyl-3-phenylazetidin-2-ones with substitutions on the aromatic ring, *Farmaco* 28(2), 105-15.

Gust, D. et al. (1987) Charge separation in carotenoporphyrin-quinone triads: synthetic, conformational, and fluorescence lifetime studies, *J. Am. Chem. Soc.* 109(3), 846-56.

Hama, T.; Hartwig, J. F. (2008) Palladium-catalyzed alpha-arylation of esters with chloroarenes, *Org. Lett.* 10(8), 1549-52.

Jiang, Z. et al. (2012) Catalytic Diastereoselective Tandem Conjugate Addition-Elimination Reaction of Morita-Baylis-Hillman C Adducts by C—C Bond Cleavage, *Chem. Asian J.* 7(4), 771-7.

Jorgensen, M.; Lee, S.; Liu, X.; Wolkowski, J. P.; Hartwig, J. F. (2002) Efficient Synthesis of α-Aryl Esters by Room-Temperature Palladium-Catalyzed Coupling of Aryl Halides with Ester Enolates, *J. Am. Chem. Soc.* 124(42), 12557-65.

Joseph-Nathan, P.; Massieu, G. (1978) γ-Hydroxy-γ-phenyl-caproamide, an anticonvulsant molecule, *Revista. Latinoamer. Quim.* 9(2), 90-2.

Kato, D., Mitsuda, S., Ohta, H. (2003) Microbial deracemization of alpha-substituted carboxylic acids: substrate specificity and mechanistic investigation. *J. Org. Chem.*, 68(19), 7234-42.

Kitamura, M.; Murakami, K., Shiratake, Y.; Okauchi, T. (2013) Synthesis of α-arylcarboxylic acid amides from silyl enol ether via migratory amidation with 2-azido-1,3-dimethylimidazolinium hexafluorophosphate, *Chem. Lett.* 42(7), 691-3.

Kolonko, K. J.; Reich, H. J. (2008) Stabilization of ketone and aldehyde enols by formation of hydrogen bonds to phosphazene enolates and their aldol products, *J. Am. Chem. Soc.* 130(30), 9668-9.

Koltunov, K. Yu., Walspurger, S.; Sommer, J. (2004) Superacidic activation of α,β-unsaturated amides and their electrophilic reactions, *Eur. J. Org. Chem.* 4039-47.

Krall, R. L., Penry, J. K., White, B. G., Kupferberg, H. J., and Swinyard, E. A. (1978) Antiepileptic drug development: II. Anticonvulsant drug screening. *Epilepsia* 19, 409-428.

Krivoshein (2016a) Anticonvulsants based on the α-substituted amide group pharmacophore bind to and inhibit function of neuronal nicotinic acetylcholine receptors, *ACS Chem. Neurosci.* 7: 316-326.

Krivoshein (2016b) Antiepileptic drugs based on the α-substituted amide group pharmacophore: from chemical crystallography to molecular pharmaceutics, *Curr. Pharm. Des.* 22: 5029-5040.

Kushner, S.; Cassell, R. I.; Morton, J., II, Williams, J. H. (1951) Anticonvulsants. *N*-Benzylamides, *J. Org. Chem.* 16, 1283-8.

Lenkowski, P. W., et al. (2004) Block of human NaV1.5 sodium channels by novel alpha-hydroxyphenylamide analogues of phenytoin. *Eur. J. Pharm. Sci.* 21(5), 635-44.

Marshall, F. J. (1958) 3,3-Disubstituted-2-pyrrolidinones, *J. Org. Chem.* 23, 503-5.

Meyer, R. B., Hauser, C. R. (1961) Alkylations at the α-carbon of phenylacetamide and phenylacetic acid through their disodio salts, *J. Org. Chem.* 26, 3696-8.

Meza-Toledo, S. E. et al. (1990) A new homologous series of anticonvulsants: phenyl alcohol amides. Synthesis and pharmacological evaluation, *Arzneimittelforschung* 40(12), 1289-91.

Meza-Toledo, S. E., Ortega-Gonzalez, C.; Juarez-Carvajal, E.; Carvajal-Sandoval, G. (1995) Stereoselective anticonvulsant activity of the enantiomers of (+/−)-2-hydroxy-2-phenylbutyramide. *Arzneimittelforschung,* 45(7), 756-9.

Meza-Toledo, S. E.; Juarez-Carvajal, E.; Carvajal-Sandoval, G. (1998) Synthesis of a new homologous series of p-chlorophenyl alcohol amides, their anticonvulsant activity and their testing as potential GABAB receptor antagonists, *Arzneimittelforschung* 48(8), 797-801.

Meza-Toledo, S. E., *Olea*-Gomez, A., Mora-Ramirez, E. Y., Peralta-Cruz, J., Nogueron-Chirinos, J. B. (2004) Synthesis and pharmacological evaluation of some DL-dichlorophenyl alcohol amides anticonvulsants, *Arzneimittelforschung* 54(12), 830-4.

Meza-Toledo, S. E. et al. (2008a) Synthesis of DL-fluorobenzenamides as anticonvulsants. *Arzneimittelforschung* 58(4), 155-9.

Meza-Toledo S. E. et al. (2008b) Synthesis of DL-hydroxybenzenamides as anticonvulsants. *Arzneimittelforschung* 58(3), 105-10.

Mijin, D. Z. et al. (2000) Conformation of N-substituted 2-Phenylbutanamides, *Facta Universitatis* (Physics, Chemistry and Technology) 2, 109-13.

Nilsson, B. M.; Vargas, H. M.; Ringdahl, B.; Hacksell, U. (1992) Phenyl-substituted analogues of oxotremorine as muscarinic antagonists, *J. Med. Chem.* 35(2), 285.

Pagliarini, G., Cignarella, G., Testa, E. (1966) Chemical investigations on the behavior of phenylbutyrolactones. I. Synthesis of alpha-phenyl-gamma-aminobutyric acid and of 3-phenylpyrrolidin-2-one of alpha-phenyl-gamma-butyrolactone. New method of synthesis of 1-aminopyrrolidin-2-ones, *Farmaco* 21(5), 355-69.

Pettersson, K. (1956) Configurational studies in the α-phenyl carboxylic acid series, *Arkiv foer Kemi* 9, 509-18.

Reddy, P. A. et al. (1996) 3,3-Dialkyl- and 3-alkyl-3-benzyl-substituted 2-pyrrolidinones: a new class of anticonvulsant agents. *J. Med. Chem.* 39(9), 1898-906.

Roufos, I., Sheryl, H., Schwarz, R. D. (1996) A structure-activity relationship study of novel phenylacetamides which are sodium channel blockers, *J. Med. Chem.* 39(7), 1514-20.

Schenck, H. A., et al. (2004) Design, synthesis and evaluation of novel hydroxyamides as orally available anticonvulsants, *Bioorg. Med. Chem.* 12(5), 979-93.

Shindikar, A. V., Khan, F., Viswanathan, C. L. (2006) Design, synthesis and in vivo anticonvulsant screening in mice of novel phenylacetamides, *Eur. J. Med. Chem.* 41(6), 786-92.

Takamatsu, K.; Hirano, K.; Satoh, T.; Miura, M. (2015) Synthesis of indolines by copper-mediated intramolecular aromatic C—H amination. *J. Org. Chem.* 80(6) 3242-9.

Volwiler, E. H.; Tabern, D. L. (1936) Some alkyl- and arylamides and ureides as hypnotics, *J. Am. Chem. Soc.* 58, 1352-4.

Wang, S. et al. (2001) Pharmacophore-based discovery, synthesis, and biological evaluation of 4-phenyl-1-arylalkyl piperidines as dopamine transporter inhibitors, *Bioorg. Med. Chem. Lett.* 11(4), 495-500.

Yin, Z. et al. (2015) Synthesis of functionalized γ-lactone via Sakurai exo-cyclization/rearrangement of 3,3-bis(silyl) enol ester with a tethered acetal. *Org. Lett.* 17: 1553-6.

Zhang, M. et al. (2016) Highly enantioselective [3+2] coupling of cyclic enamides with quinone monoamines promoted by a chiral phosphoric acid, *Chem. Commun.* 52(56): 8757-60.

Zhu, Y.; Gong, J.; Wang, Y. (2017) Free-Radical-Promoted Copper-Catalyzed Decarboxylative Alkylation of α,β-Unsaturated Carboxylic Acids with $ICH_2CF_3$ and Its Analogues. *J. Org. Chem.*, 82(14), 7428-7436.

What is claimed is:

1. A method of reducing the risk of seizures resulting from epilepsy in a patient in need thereof, comprising:

administering to the patient a pharmaceutical composition comprising a therapeutically effective amount of a compound having a structure of:

wherein $R_1$ and $R_2$ are $CH_3$, $R_5$ is F, and $R_3$, $R_4$, $R_6$ and $R_7$ are H, and pharmaceutically acceptable salts, co-crystals, and prodrugs thereof, and a pharmaceutically acceptable excipient, adjuvant, carrier, buffer, stabilizer, or mixture thereof.

2. A method of reducing the risk of seizures resulting from nerve agent poisoning in a patient in need thereof, comprising:

administering to the patient a pharmaceutical composition comprising a therapeutically effective amount of a compound having a structure of:

wherein $R_1$ and $R_2$ are $CH_3$, $R_5$ is F, and $R_3$, $R_4$, $R_6$ and $R_7$ are H, and pharmaceutically acceptable salts, co-crystals, and prodrugs thereof, and a pharmaceutically acceptable excipient, adjuvant, carrier, buffer, stabilizer, or mixture thereof.

* * * * *